United States Patent [19]

Igaki et al.

[11] Patent Number: 5,088,817
[45] Date of Patent: Feb. 18, 1992

[54] BIOLOGICAL OBJECT DETECTION APPARATUS

[76] Inventors: Seigo Igaki, Hirao-jutaku 59-103, 474, Hirao, Inagi-shi, Tokyo 206; Takashi Shinzaki, Fujitsu-atsugiryo 305, 2-3-10, Sakae-cho, Atsugi-shi, Kanagawa 243; Fumio Yamagishi, 5-541, 40-1, Ohya, Ebina-shi, Kanagawa 243-04; Ikeda: Hiroyuki, 1-7, Mugita-cho, Naka-ku, Yokohama-shi, Kanagawa 231, all of Japan

[21] Appl. No.: 437,899

[22] Filed: Nov. 17, 1989

[30] Foreign Application Priority Data

Nov. 25, 1988 [JP] Japan ................................. 63-298922
Mar. 31, 1989 [JP] Japan ................................. 1-081901
May 23, 1989 [JP] Japan ................................. 1-129515
Aug. 31, 1989 [JP] Japan ................................. 1-223256

[51] Int. Cl.⁵ ............................................. G06K 9/74
[52] U.S. Cl. ................................... 356/71; 250/556
[58] Field of Search ................ 356/71, 445, 448; 250/556; 340/825.34, 825.31, 540; 382/3, 4

[56] References Cited

U.S. PATENT DOCUMENTS 4,728,186  3/1988  Eguchi et al. .................... 356/71

FOREIGN PATENT DOCUMENTS 0045915  2/1982  European Pat. Off. .
0169496  1/1986  European Pat. Off. .
0194783  9/1986  European Pat. Off. .
61-221883 10/1986  Japan .
62-074173  4/1987  Japan .

Primary Examiner—Vincent P. McGraw
Assistant Examiner—LaCharles P. Keesee

[57] ABSTRACT

An apparatus for detecting and identifying a biological object. A transparent plate has a first surface onto which a light beam is projected and a second surface onto which a biological object to be detected and identified is placed. The light beam projected toward the first plate surface is transmitted through the plate and toward the object on the second surface, from which the light beam is reflected and retransmitted through the plate toward and through the first surface thereof and received and detected by an optical detector. The detection of a biological object is confirmed by comparing the change of the wavelength characteristics of the reflected and detected light beam in a predetermined time sequence according to the object being first placed upon and then pressed upon the second surface of the transparent plate with respective, known such characteristics thereof.

18 Claims, 13 Drawing Sheets

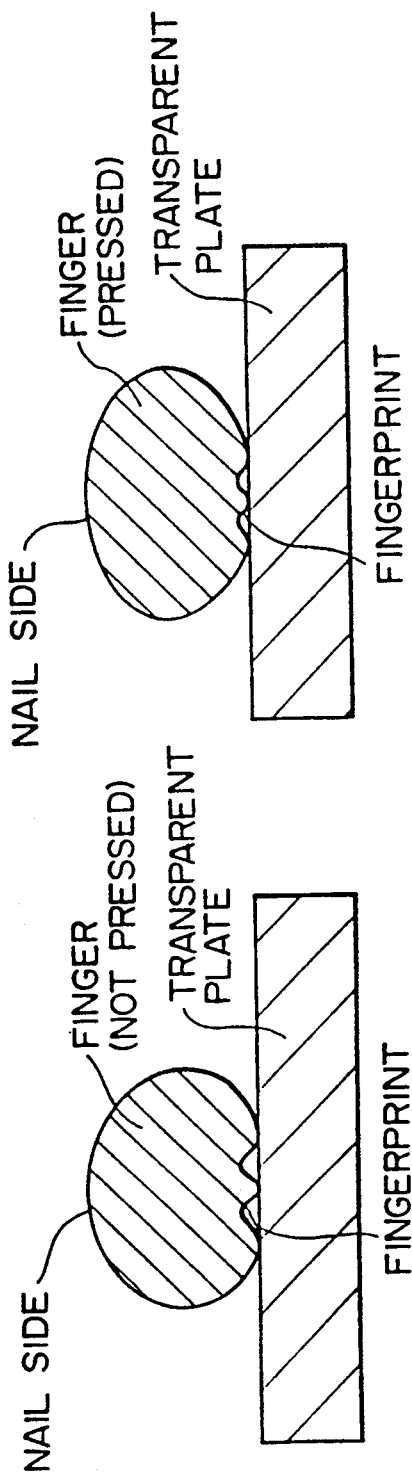
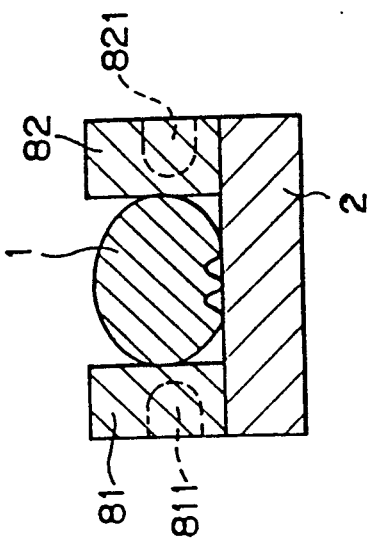
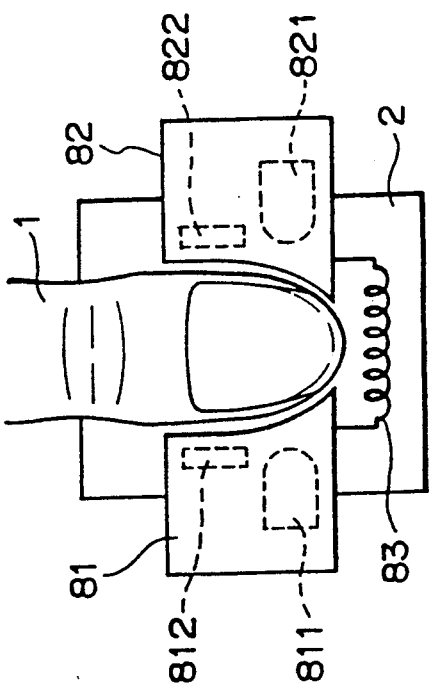
Fig. 1 PRIOR ART
Fig. 3 PRIOR ART
Fig. 4 PRIOR ART

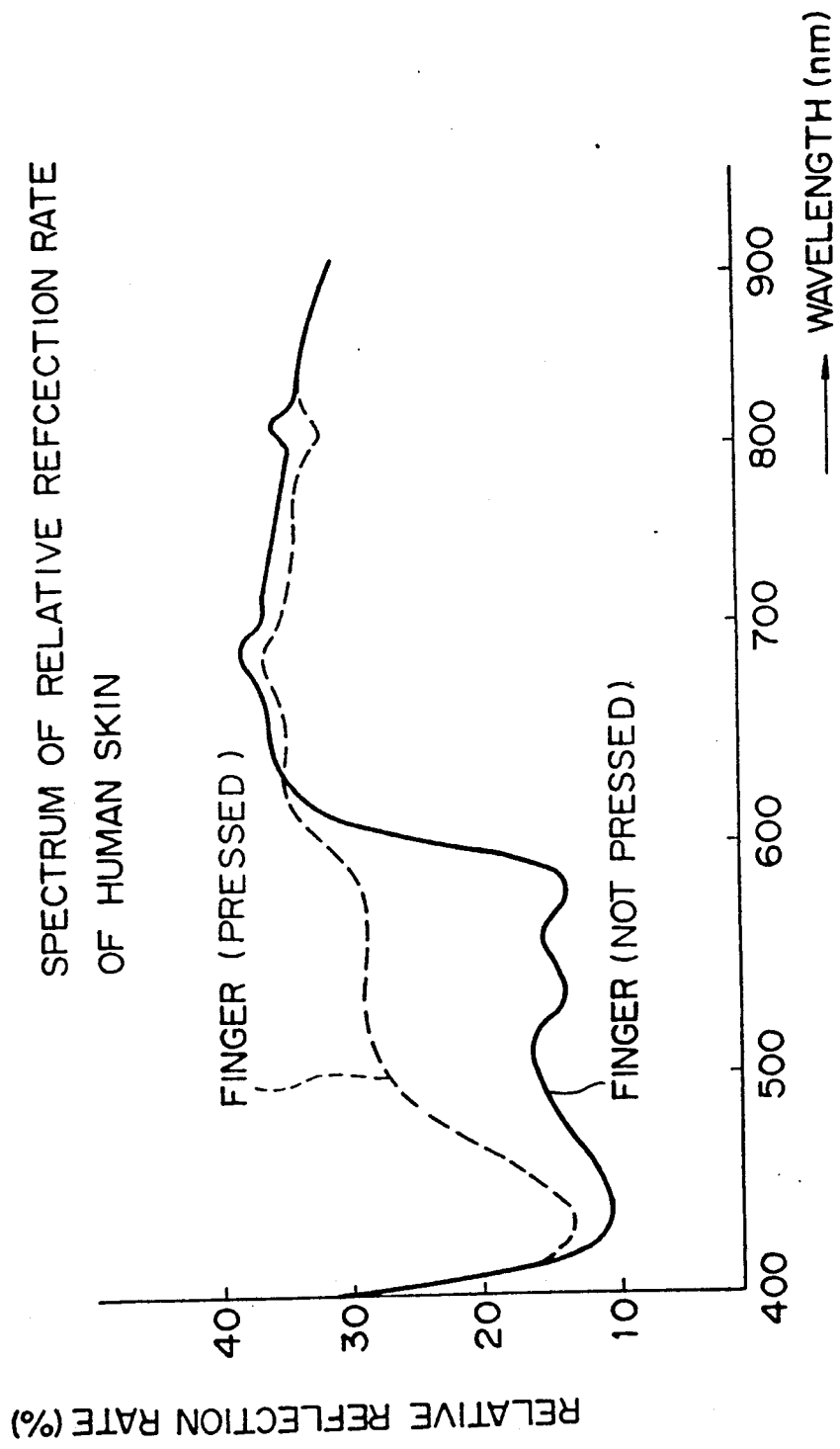

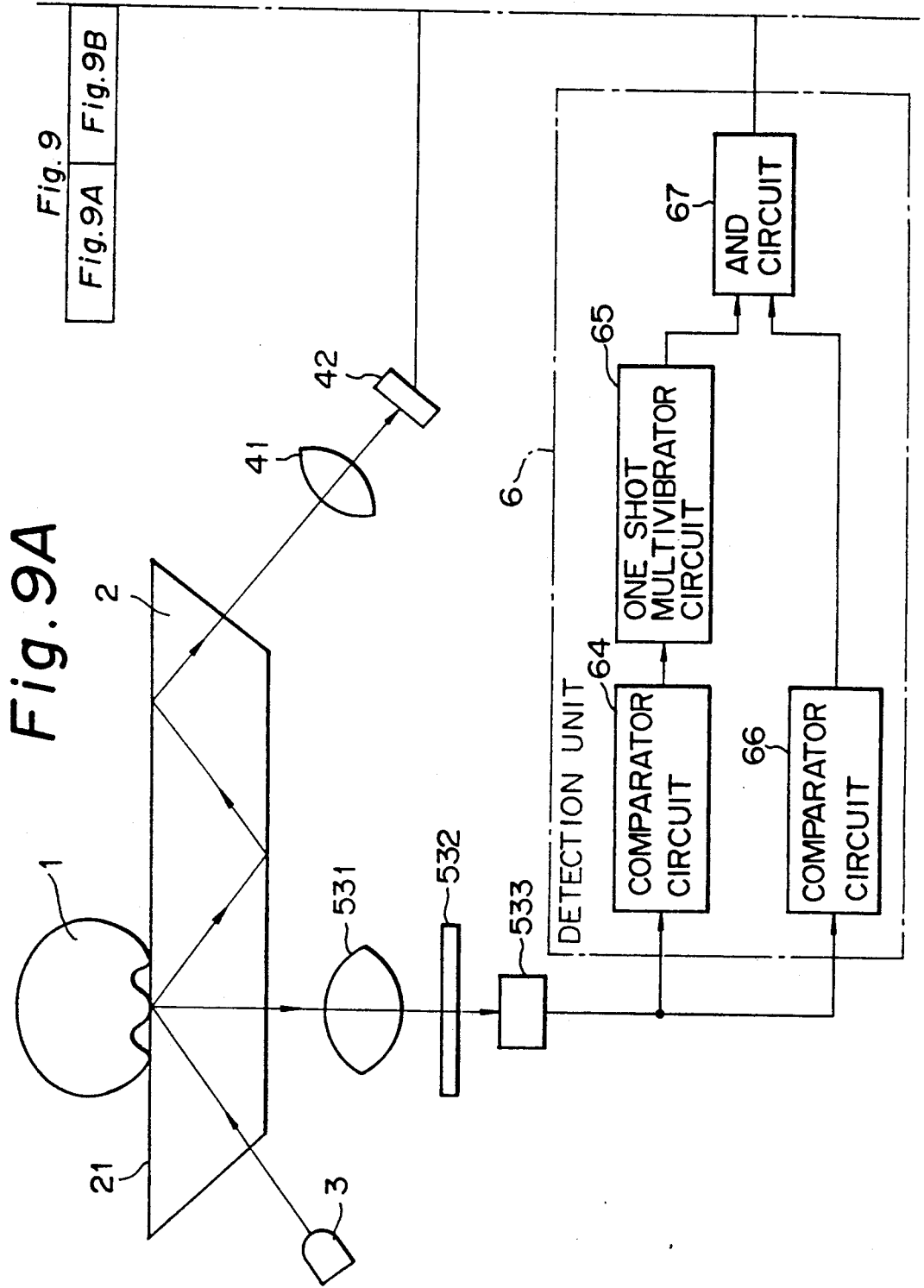

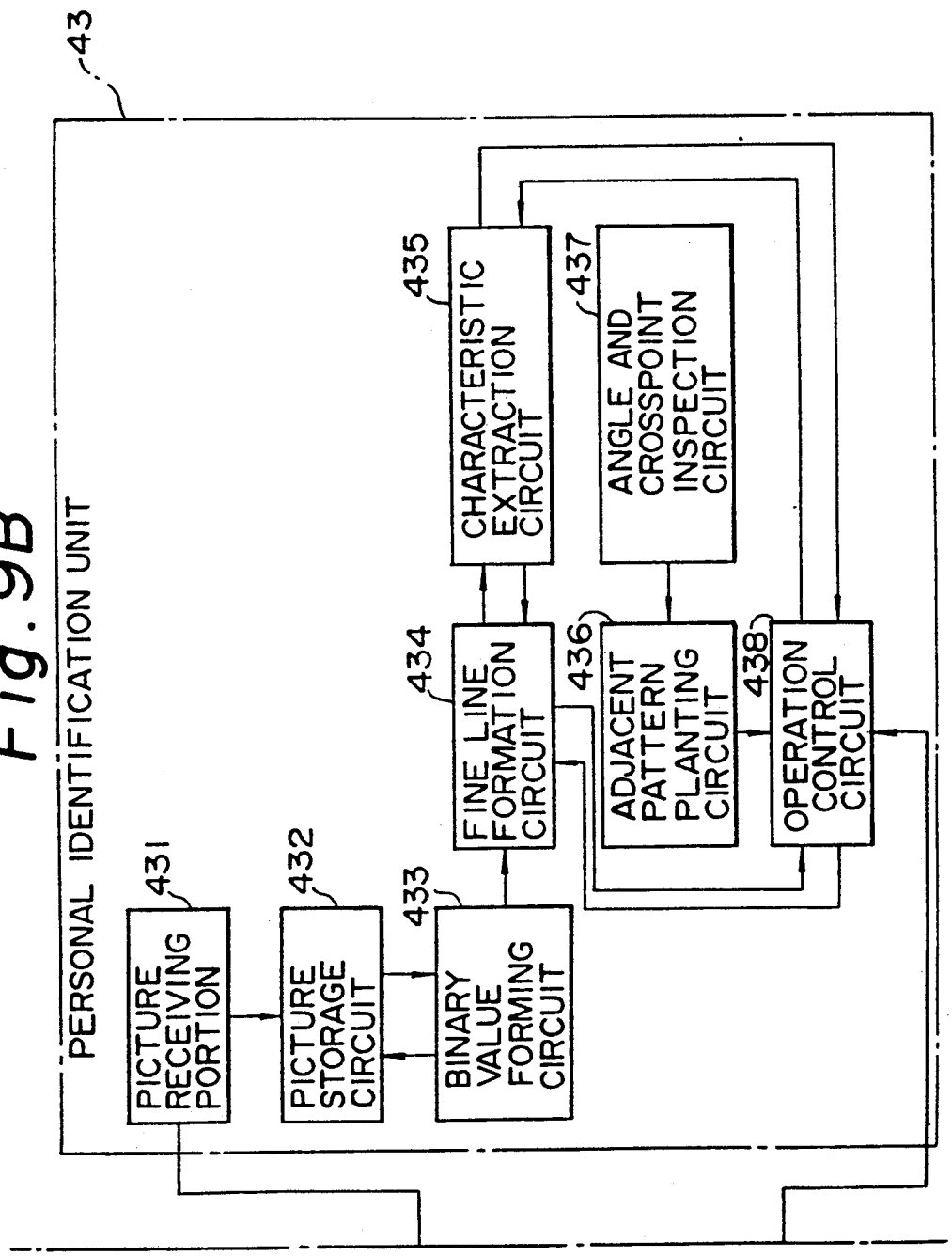

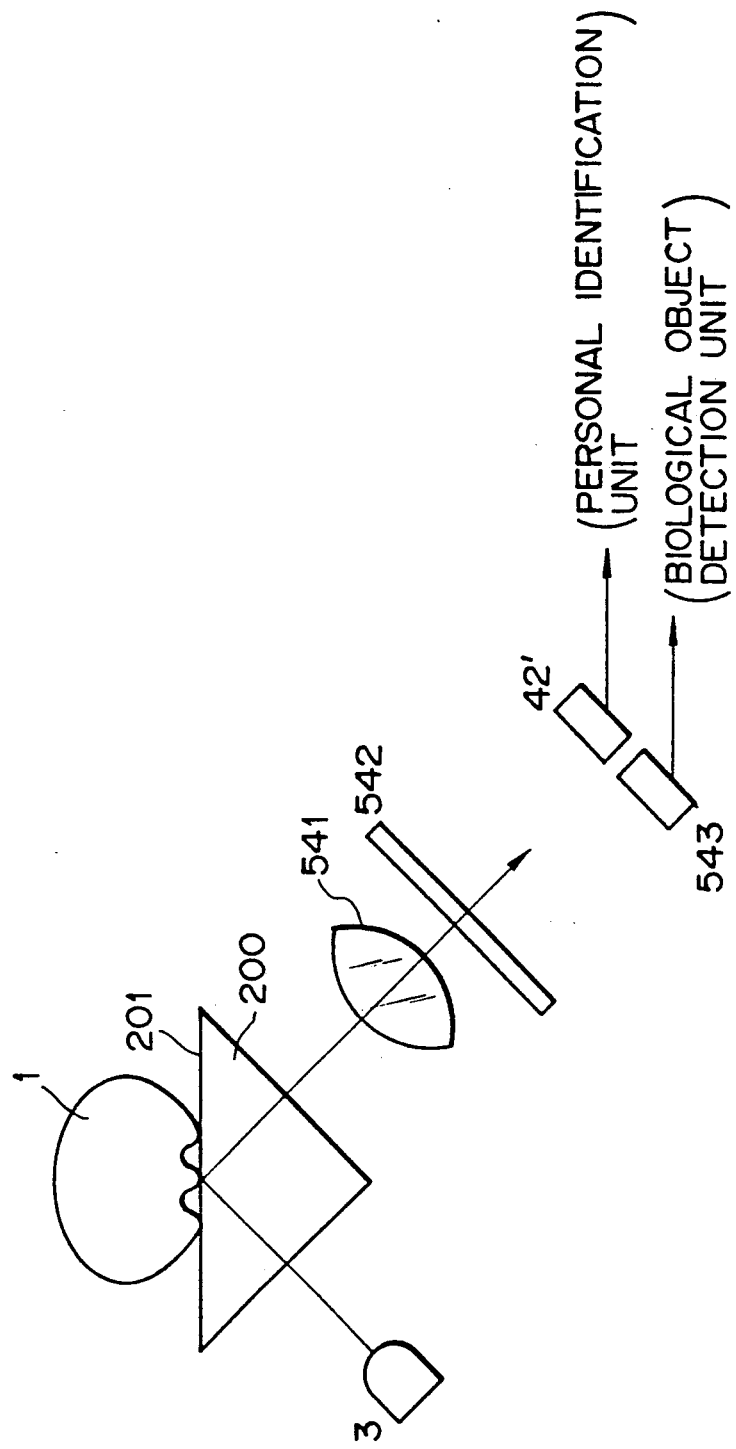

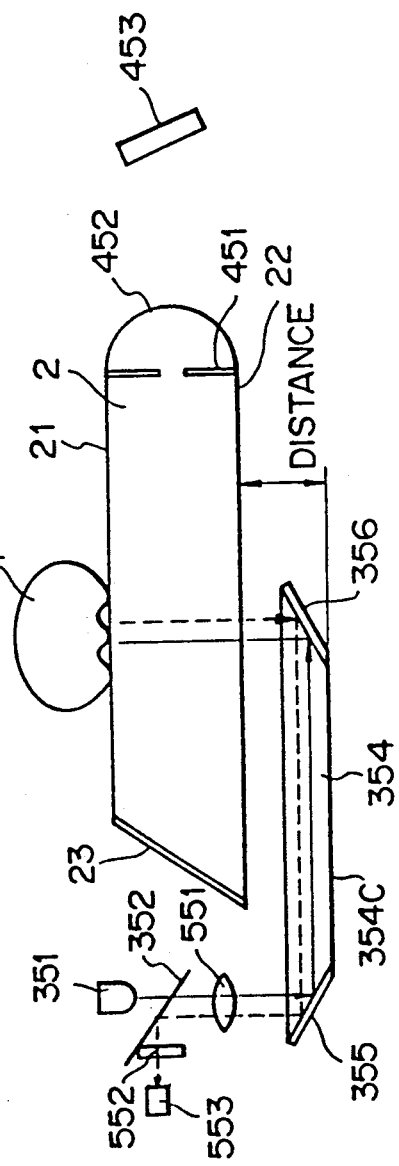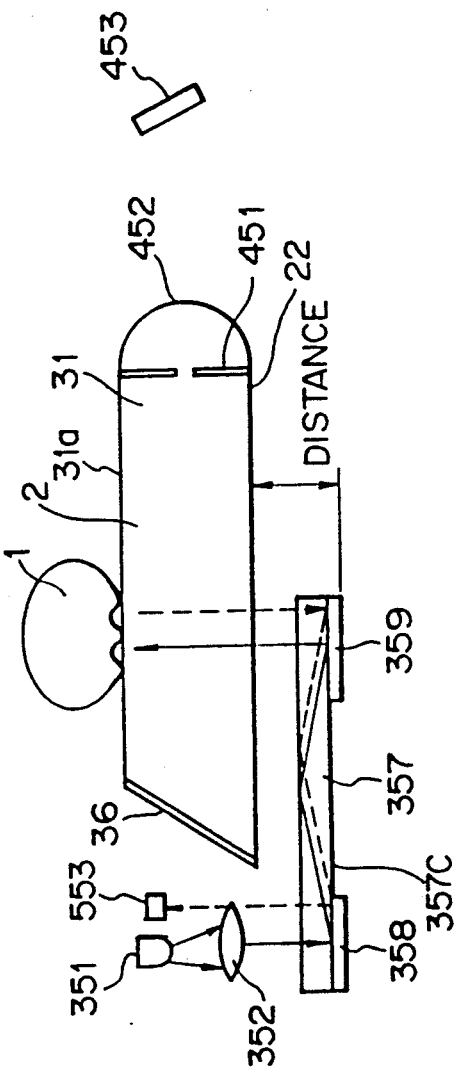

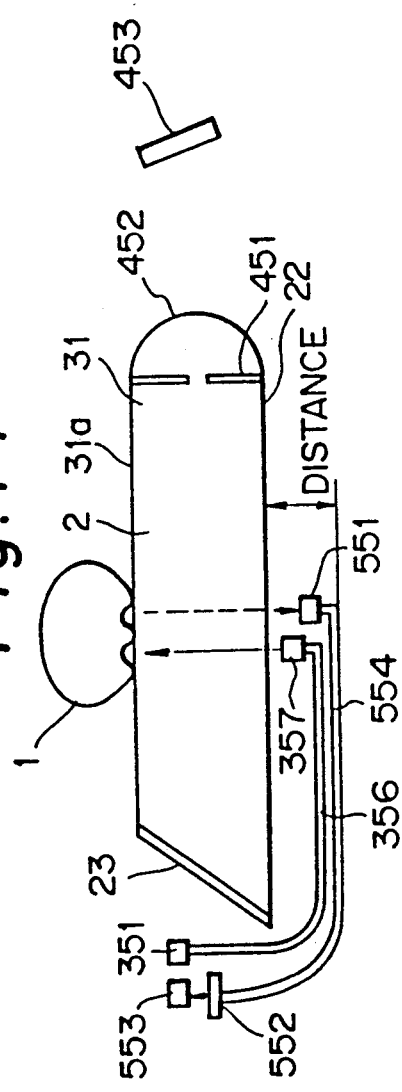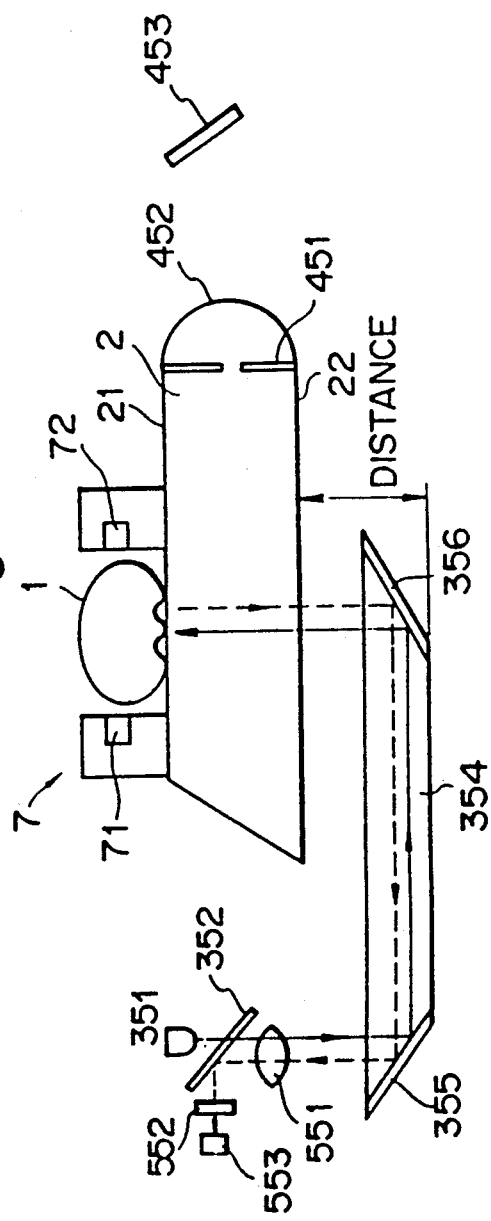

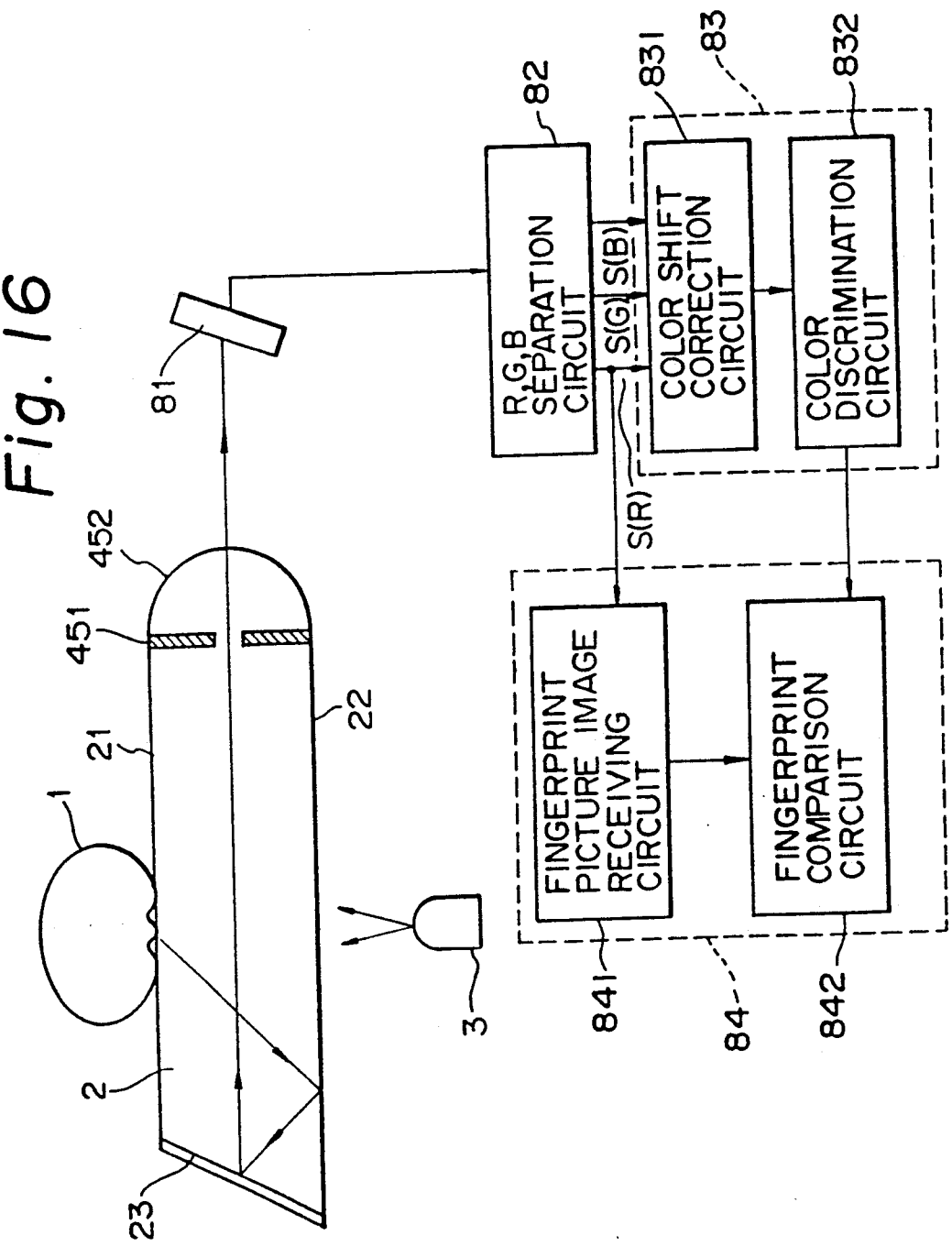

BIOLOGICAL OBJECT DETECTION APPARATUS

CROSS-REFERENCE TO RELATED APPLICATIONS

U.S. Patent application Ser. No. 07/370,768 of Masayuki KATO et al. entitled "UNEVEN-SURFACE DATA DETECTION APPARATUS" filed June 23, 1989 and U.S. Patent application Ser. No. 07/408,090 of Masayuki KATO et al. entitled "BIOLOGICAL DETECTING SYSTEM AND FINGERPRINT COLLATING SYSTEM EMPLOYING SAME" filed Sept. 14, 1989, each thereof assigned to the common assignee of the present application, Fujitsu Limited, as shown by the assignment records of the United States Patent and Trademark Office, are related to the invention of the present, new U.S. patent application.

BACKGROUND OF THE INVENTION

1. Field of the Invention

The present invention relates to an apparatus for detecting a biological object. The apparatus according to the invention is used for a personal identification system in which a person is identified by identifying a fingerprint of the person.

In a personal identification system using fingerprint identification, a fingerprint sensor is provided for reading a fingerprint, as a picture image, of a person, and a processing device for generating reference data from the picture signal read by the fingerprint sensor, registering the generated reference data, and comparing the picture signal read by the fingerprint with the reference data to identify whether or not the fingerprint belongs to an authorized person. In such a personal identification system, the fingerprint sensor must read the fingerprint picture image clearly and correctly without distortion.

In general, in a fingerprint sensor, a detection light is irradiated at a preselected angle onto the ridge line portions and the groove line portions of the fingerprint pressed against a light conducting plate (a transparent plate), through this transparent plate. According to Snell's law, only light reflected from the ridge line portions of fingerprint is transmitted by the full reflection inside thereof through the transparent plate to reach a light receiving element and produce a fingerprint picture electrical signal. The light reflected from the groove line portions of fingerprint is not transmitted by such a full reflection, and thus such an electrical signal is not produced.

In such a fingerprint sensor, a fraudulent operation of the fingerprint identification system having such a biological object detection means, with criminal intention, can be carried out by using a replica of a human finger, made of rubber or plaster, and therefore, protection from fraudulent use of the personal identification system by a false identification of a fingerprint by the fingerprint sensor was required.

A number of attempts have been made to provide such protection against a fraudulent operation of the fingerprint sensor. For example, a pulsating electrical signal corresponding to the pulsation of the blood flow in the human finger is derived from a light receiver receiving light irradiated from a light emitter and transmitted through the finger to identify the fingerprint thereof.

In another example, an electric current corresponding to the skin resistance of a human finger is measured by an electrical circuit formed by a pair of electrically conductive electrodes against which the human finger is pressed. In a further example, a change with time of the degree of contact between the surface of the human fingerpad (the palm side of a human fingertip) and the surface of the transparent plate for the fingerprint detection, which is affected by perspiration from the surface of the human fingerpad, is detected by an electrical signal output from the light receiver. Nevertheless, these attempts at protection against fraudulent operation were not successful, because a considerable length of time is required for the detection or a very precise detection cannot be obtained, and thus practical use of the above attempts was not adequate.

A prior art fingerprint sensor having a biological object discriminating means has been proposed, in which the nature of the skin of a living human fingerpad, i.e., that the spectral reflectance of the skin of a living human fingerpad to which a pressure is applied is different from that of a non-living object such as a replica finger, is utilized.

The color of the skin of a finger not under pressure is usually reddish, but becomes whitish when a pressure is applied to the skin of the finger by, for example, pressing the fingerpad against a plate. It has been acknowledged that the spectral reflectance of the light in the red spectral range, i.e., the light wavelength of approx. 640 to 770 nm, does not show a substantial difference between the pressed state and the not pressed state, and the spectral reflectance of the light in the blue and green spectral range, i.e., the light wavelength of approx. 400 to 600 nm, in the not pressed state is much less than in the pressed state. Accordingly, by measuring the spectral reflectance in the blue and green spectral range of the surface of an object in question, it is possible to detect whether or not this object is a biological object.

In this prior art biological object detection means there is provided a finger nipping member constituted by a pair of nip elements for nipping the tip of a finger therebetween, and a spring bridging these nip elements for developing a force to cause these nip elements to be biased toward each other. Each nip element is provided with a light emitting element for emitting a light having a spectral wavelength range including the blue or green range, and a light sensing element for responding to a light having the spectral wavelength range of blue or green.

Namely, when a fingertip is forced into the gap between these nip elements against the force of the spring thereof, the gap between these nip element is enlarged and thus pressure is applied to the sides of the fingertip by the action of the spring. As the pressure applied to the sides of the fingertip increases, the color of the skin of the finger changes from reddish to whitish, to thus change the spectral reflectance, and accordingly, the value of the light having the spectral wavelength of the blue and green ranges detected by the light sensing element is increased. Therefore, the biological object detection is carried out by using the result of the detection of the reflected blue or green range light by the light sensing element.

Nevertheless, a fraudulent operation of the fingerprint identification system having such a biological object detection means can be carried out by lo using a first replica of a finger for counterfeiting a human fingerprint and the spectral reflectance characteristic of human finger skin in the pressed state and a second replica of a finger for counterfeiting the spectral reflectance characteristic of human finger skin in the not-pressed state. The fraudulent operation is carried out by, first forcing the first replica of a finger covered by the second replica of a finger into the space between the above-described nip elements to imitate the human finger in the not-pressed state, and second, taking the second replica of a finger out of the first replica of a finger to imitate the human finger in the pressed state. Accordingly, protection of the personal identification system by fingerprint identification against such fraudulent operation of the fingerprint sensor is urgently required.

SUMMARY OF THE INVENTION

An object of the invention is to provide an improved apparatus for detecting a biological object based on changes in a color of the surface of a biological object due to a pressure applied to the biological object by a biological object discrimination means, using the light reflection on the fingerprint surface of a finger to prevent a fraudulent operation of a fingerprint sensor and enhance the security and reliability of the biological object detecting apparatus.

According to the invention, there is provided an apparatus for detecting a biological object based on changes in a color of a surface of a biological object du to a pressure applied to the biological object when the biological object is pressed onto a transparent plate, the apparatus comprising: a transparent plate, onto which an object to be detected is placed, for allowing the passage of projected light and reflected light used for an optical detection; a light source located under the transparent plate for projecting a light beam used for a biological object detection toward a portion of the surface of the placed object toward which a light beam for detecting a characteristic pattern of the surface of the placed object is directed; and a light detection unit located below the transparent plate for receiving the light projected from the light source and subsequently reflected by the..surface of the object alternatively when placed on or pressed onto the transparent plate and detecting the corresponding characteristics of the reflected received light. The detection of whether or not the detected object is a biological object is based on the detection of the characteristic of the reflection rate of the received light by the light detection unit.

BRIEF DESCRIPTION OF THE DRAWINGS

In the drawings,

FIG. 1 and FIG. 2 illustrate a prior art principle of detection of a biological object;

FIG. 3 and FIG. 4 show an example of a prior art apparatus for detecting a biological object;

FIG. 9 shows the combination of FIGS. 9A and 9B which together illustrate an apparatus for detecting a biological object according to still another embodiment of the present invention;

FIG. 11 shows an apparatus for detecting a biological object according to still another embodiment of the present invention; and FIGS. 12, 13, 14, 15, and 16 show apparatuses for detecting a biological object according to further embodiments of the present invention.

DESCRIPTION OF THE PREFERRED EMBODIMENTS

Figure 5:
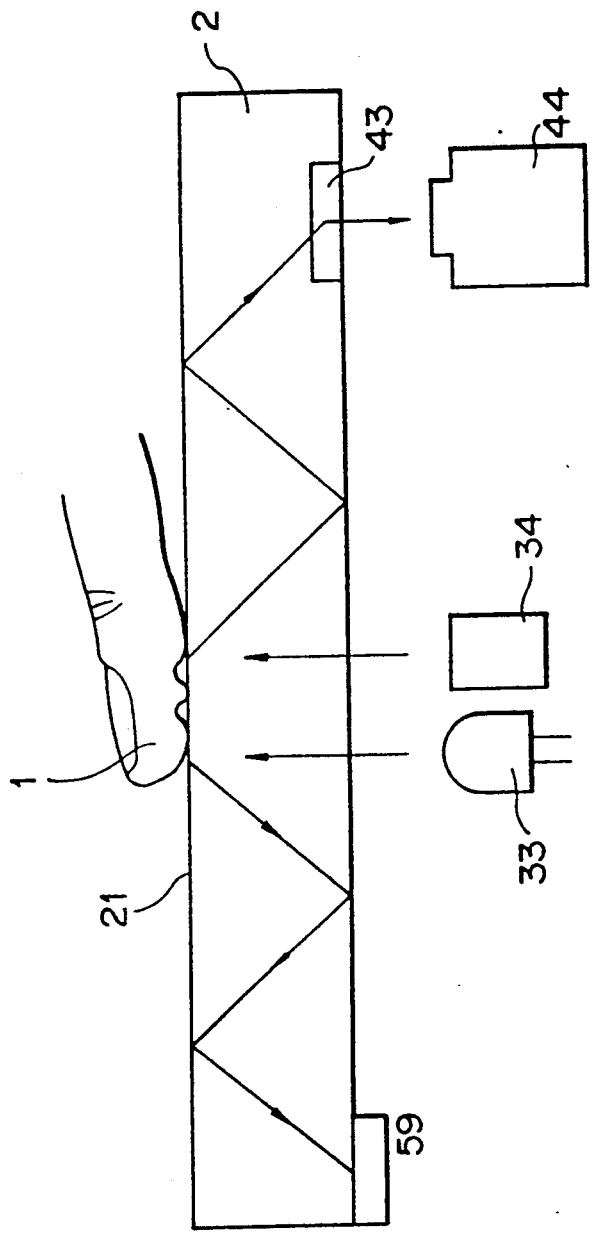
FIG. 5 shows another example of a prior art apparatus for detecting a biological object.

Before describing the preferred embodiments of the present invention, prior art apparatuses for detecting a biological object associated with a personal identification system in which a person is identified by identifying a fingerprint of the person are described with reference to FIG. 1 to FIG. 5.

The principle of the detection of a biological object used in a prior art is illustrated in FIG. 1 and FIG. 2. In FIG. 1, a human finger is illustrated as a cross-section with the upper nail side and the lower fingerprint side. The color of the skin of a human finger not under pressure, as shown in the left of FIG. 1, is usually reddish, but becomes whitish when a pressure is applied to the skin of the finger by, for example, pressing the finger to a plate as shown in the right of FIG. 1. It has been acknowledged that the spectral reflectance of the light in the red spectral range, i.e., the light wavelength of approx. 640 to 770 nm, does not show a substantive difference between the pressed state and the not-pressed state, but the spectral reflectance of the light in blue and green spectral range, i.e., the light wavelength of approx. 400 to 600 nm in the not-pressed state is much smaller than in the pressed state as shown in FIG. 2. Therefore, by measuring the spectral reflectance in the blue and green spectral range of the surface of an object in question, it is possible to detect whether or not this object is a biological object.

A prior art apparatus for detecting a biological object is shown in FIG. 3 and FIG. 4. FIG. 3 is a top view and FIG. 4 is an elevation view. As shown in FIG. 3, a finger nipping member is constituted by a pair of nip elements 81, 82 for nipping the tip of a finger 1 therebetween and a spring 83 bridging these nip elements 81, 82 for biasing these nip elements 81, 82 toward each other. The nip elements 81, 82, contain light emitting elements 811, 821, and light sensing elements 812, 822. Each of the light emitting elements 811, 821 emits light including the blue or green light wavelength, and each of the light sensing elements 812, 822 is sensitive to the light having the blue or green light wavelength. Each of the light emitting elements 811, 821 may be a light emitting element which emits the white light.

When a fingertip is forced into the gap between the nip elements 81 and 82, the gap between the nip elements 81 and 82 is enlarged and a pressure is applied to the sides of the fingertip by the action of the spring 83. As the pressure applied to the sides of the finger tip increases, the color of the skin of the finger changes from reddish to whitish, to thereby change the spectral reflectance thereof, and accordingly, the value of the light having the spectral wavelength of the blue and green ranges detected by the light sensing elements 812, 822 is increased. Accordingly, the biological object detection is carried out by using the result of the detection of the reflected blue or green range light by the light sensing elements 812, 822. This prior art apparatus, however, cannot prevent a fraudulent operation of the fingerprint identification system by sing replicas of a finger. The apparatus of this type for detecting a biological object is disclosed, for example, in Japanese Unexamined Patent Publication (Kokai) No. 61-221883 corresponding to U.S. Pat. No. 4,728,186.

Another prior art apparatus for detecting a biological object is shown in FIG. 5. As shown in FIG. 5, the apparatus is constituted by a light conducting plate (a transparent plate) 2, a green light emitting element 33 for biological object detection, a light sensor element 59 for biological object detection, a laser emitting element 34, a hologram element 43, for fingerprint detection, and a light sensor element 44 for fingerprint detection. In the apparatus, the green light having a spectral wavelength of approx. 450 to 570 ns, emitted from the green light emitting element 33, is reflected at the surface of the finger 1 pressed against the surface 21 of the plate 2, and the reflection light is transmitted through the plate 2 in accordance with the principle of a full reflection filtering, to the light sensor element 59. Based on the difference of the reflectance of the skin of the fingerpad in the state in which the flow rate of blood is low and in the state in which the flow rate of blood is high, due to the pulsation of the blood flow in the human finger, it is possible to detect the biological object from the reflected light detected by the light sensor element 59. After the detection of the biological object, the fingerprint detection is carried out by using the laser emitting element 34, a hologram element 43, and the light sensor element 44.

Nevertheless, this prior art apparatus is not successful because a considerable length of time is required for the detection. The apparatus of this type is disclosed, for example, in Japanese Unexamined Patent Publication (Kokai) No. 62-74173.

((Embodiment of FIG. 6))

Figure 6:
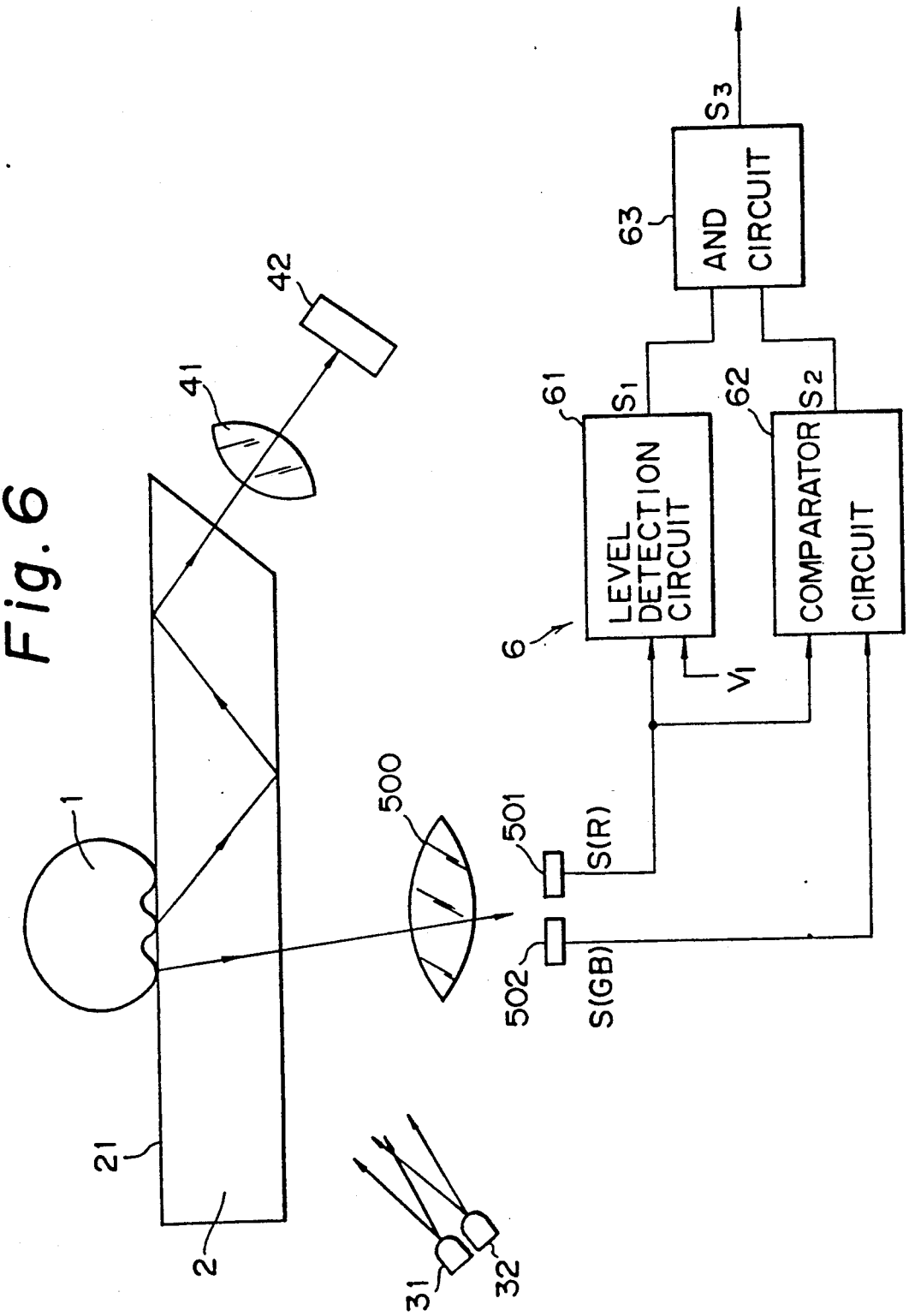
FIG. 6 shows an apparatus for detecting a biological object according to an embodiment of the present invention.

An apparatus for detecting a biological object according to an embodiment of the present invention is shown in FIG. 6. The apparatus of FIG. 6 is provided with a transparent plate 2 able to conduct light and having an inspection surface 21 on which a finger 1 to be identified is placed, a light emitting element 31 for biological object detection, a light emitting element 32 for fingerprint picture image detection, an optical lens 41, a light sensing element 42 for fingerprint picture image detection, an optical lens 500, light sensing elements 501 and 502, and a detection unit 6 having a level detection circuit 61, a comparator circuit 62, and an AND circuit 63. The optical lens 500, the light sensing elements 501 and 502, and the signal processing unit 6 are used specifically for the biological object detection.

It is possible to incorporate the light emitting element 31 for biological object detection and the light emitting element 32 for fingerprint picture image detection into a single light emitting element.

The light sensing element 501 responds to the light of the red spectral wavelength range of approx. 640 to 770 nm, to generate a signal S(R) which corresponds to this light of the red spectral wavelength range. The light sensing element 502 responds to the light of the spectral wavelength range shorter than that of the red spectral wavelength, such as the green spectral wavelength range of approx. 490 to 550 nm, the blue spectral wavelength range of approx. 430 to 490 nm, or a combination of these green and blue spectral wavelength ranges, to generate a signal S(GB) which corresponds to this light of the green, blue, or green-blue combination spectral wavelength range.

In the level detection circuit 61, which is constituted by an analog comparator such as a window comparator, the signal S(R) is compared with a predetermined reference value $V_1$, and when the signal S(R) is greater than the reference value $V_1$, an instruction signal $S_1$ is produced. The instruction signal $S_1$ represents the detection of the contact of a finger 1 with the glass plate 2. The value of $V_1$ is selected as a value slightly smaller than the level of the reflected light based on the reflectance of the skin of a human finger in the red spectral wavelength range, in both the pressed state and the not-pressed state, In the comparator circuit 62, the signal S(R) is compared with the signal S(GB) - S(GB)" becomes smaller as a result of the pressed state, than the value of "S(R) - S(GB)" as was produced in the not-pressed state, the signal $S_2$, which represents a color change of an object under detection, is produced.

In the AND circuit 63, when both signals $S_1$ and $S_2$ are received, a biological object determination signal $S_3$ is produced, and the produced signal $S_3$ is supplied to a fingerprint picture image processing device (not shown) to allow, or enable registration and comparison operations of ,the fingerprint picture image to be carried out.

The operation of the apparatus of FIG. 6 will be described. First, a person to be identified places, i.e., gently presses, a finger 1 against the inspection surface 21 of the plate 2. In this state, the color of the skin of the finger 1 is reddish, which corresponds to the curve shown by a solid line in FIG. 2. The reflected light from the skin of the fingerpad contains a high red light value and a low blue or green light value. The signals S(R) and S(GB) generated in the light sensor elements 501 and 502 correspond to the values shown by the solid line of FIG. 2. Since the condition $S_R > V_1$ is satisfied, the level detection circuit 61 produces the signal $S_1$, which indicates that the finger 1 is touching the inspection surface 21 of the plate 2. Note, as the finger is still only gently placed, the difference "S(R) - S(GB)" is the value for the not-pressed state and thus the signal $S_2$ is not produced in the comparison circuit 64 in this state.

Next, the person to be identified firmly presses the finger 1 against the inspection surface 21 of the plate 2. Accordingly, the color of the skin of the finger 1 becomes whitish, which corresponds to the curve shown by a broken line in FIG. 2. The reflected light from the skin of the fingerpad now contains high red, as well as high blue, and green light values; accordingly, the difference "S(R) - S(GB)" becomes smaller for the pressed state than the difference "S(R) - S(GB)" in the not pressed state, and the signal $S_2$ is produced by the comparator circuit 62. Upon receiving the signal $S_1$ from the level detection circuit 61 and the signal $S_2$ from the comparison circuit 62, the AND gate 63 produces the signal $S_3$, which indicates that the finger 1 on the plate 2 is a biological object, whereby the biological object detection of the finger under detection is carried out.

In the apparatus of FIG. 6, since the light for the biological object detection is irradiated onto the inspection surface 21 of the plate 2 against which the fingerprint of the finger 1 is pressed, and the biological object detection is carried out based on the reflected light from the skin of the fingerpad, a fraudulent operation of the fingerprint sensor having a biological object detection means by using first and second replicas of a finger, which was successful in the hereinbefore described prior art apparatus, cannot succeed in the apparatus of FIG. 6. This is because, first the formation of a counterfeit fingerprint on the second replica of finger is required, and second, the reading of the fingerprint picture images becomes impossible due to the removal of the second replica of a finger from the first replica of a finger and thus a fingerprint identification operation per se becomes impossible.

Therefore the biological object detection as carried out by the apparatus of FIG. 6, prevents the fraudulent operation of the fingerprint sensor with criminal intent.

In the fingerprint picture image detection by the apparatus of FIG. 6, it is possible to use either a prism system or a holographic system.

((Embodiment of FIG. 7))

Figure 7:
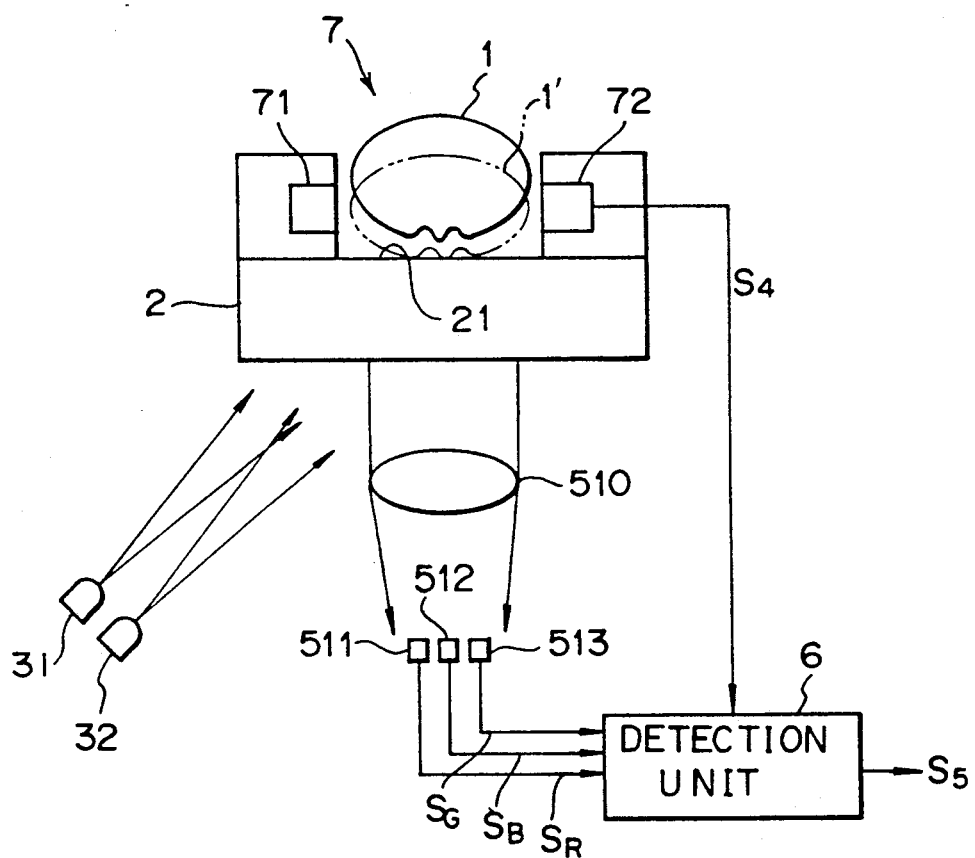
FIG. 7 shows an apparatus for detecting a biological object according to another embodiment of the present invention.

An apparatus according to another embodiment of the present invention is shown in FIG. 7. The apparatus of FIG. 7 is provided with a light switch unit 7 constituted by a light source element 71 and a light receiving element 72, a lens 510, light sensor elements 511, 512, and 513 having a red filter, blue filter, and green filter, respectively, and a detection circuit 6.

The light switch unit 7 produces a finger presence signal $S_4$ from the light receiving element 72 when a finger is placed on the inspection surface 21 of the plate 2, in either the not-pressed state 1 or in the pressed state 1'. In operation, the finger is first in the not pressed state 1, and subsequently, in the pressed state 1'.

In the detection circuit 6, the red light signal $S_R$, the blue light signal $S_B$, and the green light signal $S_G$ from the light sensor elements 511, 512, and 513 are compared when the operation of the detection circuit 6 is enabled by the finger presence signal $S_4$ from the light switch unit 7. When the relative level relationships between the signals $S_R$, $S_B$, and $S_G$ satisfy in time succession the respective characteristics for both the not-pressed finger and the pressed finger shown in FIG. 2, the biological object detection signal $S_5$ is output by the detection unit 6.

Namely, if the object in question is a human finger as a biological object, the relationship is first $S_R > S_B = S_G$, and subsequently, becomes $S_R \approx S_B \approx S_G$. If the object in question is a replica of a finger, the above relationship cannot be established.

The fingerprint picture image detection is carried out in the same manner as shown in FIG. 6, and thus the description thereof is abbreviated with regard to FIG. 7.

(( Embodiment of FIG. 8))

Figure 8:
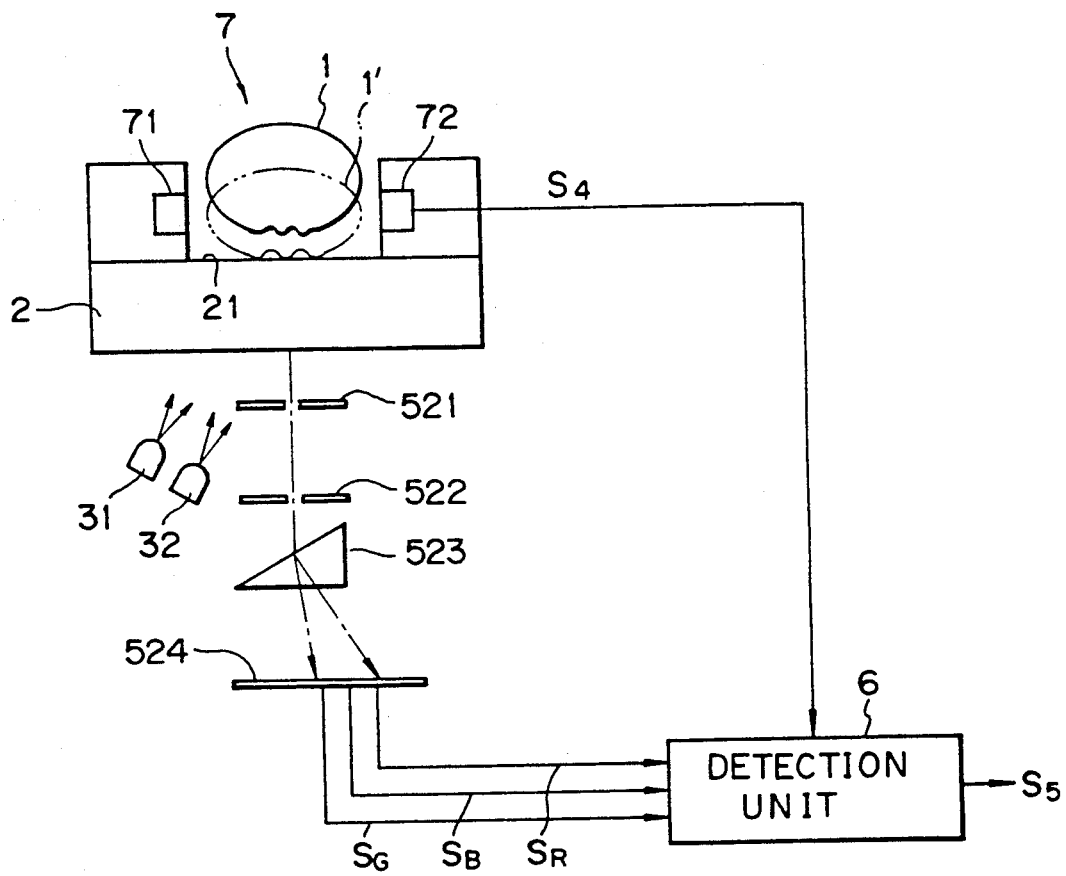
FIG. 8 shows an apparatus for detecting a biological object according to still another embodiment of the present invention.

An apparatus according to still another embodiment of the present invention is shown in FIG. 8. The apparatus of FIG. 8 is provided with a light emitting element 31 for biological object detection, slit plates 521 and 522, a prism 523, a line sensor 524, and a detection circuit 6.

The reflected light from the skin of the fingerpad is led to the prism 523 through the slits of the slit plates 521 and 522, and light beams spectrally separated by the prism 523 are led to the line sensor 524. The line sensor 524 produces the signals $S_R$, $S_B$, and $S_G$, which correspond to the red, blue, and green lights, respectively. The operations of the light switch unit 7 and the detection unit 6 are substantially the same as in the apparatus of FIG. 7, and thus description of the fingerprint picture image detection is abbreviated with regard to FIG. 8.

((Embodiment of FIGS. 9A and 9B, combined as shown in FIG. 9))

An apparatus according to still another embodiment of the present invention is shown in FIG. 9 (i.e., 9A and 9B, combined as shown in a light emitting element 3 such as a laser light source for both a biological object detection and fingerprint picture image detection, a lens 531, a filter 532, a light sensing element 533, a detection unit 6, a lens 41, a light sensing element 42, and a personal identification unit 43.

The light emitting element 3 is selected to emit a white light or a light having the green light wavelength at the center thereof, and the light sensor element 533 is selected to be sensitive to a light having the green light wavelength at the center thereof.

The detection unit 6 is constituted by a comparator circuit 64, a one shot multivibrator circuit 65, a comparator circuit 66, and an AND circuit 67. The personal identification unit 43 (FIG. 9B) comprises a picture receiving portion 431, a picture storage circuit 432, a binary value forming circuit 433, a fine line formation circuit 434, a characteristic extraction circuit 435, an adjacent pattern planting circuit 436, an angle and crosspoint inspection circuit 437, and an operation control circuit 438. The personal identification unit 43 may be constructed, for example, as a 16 bit personal computer.

Figure 10:
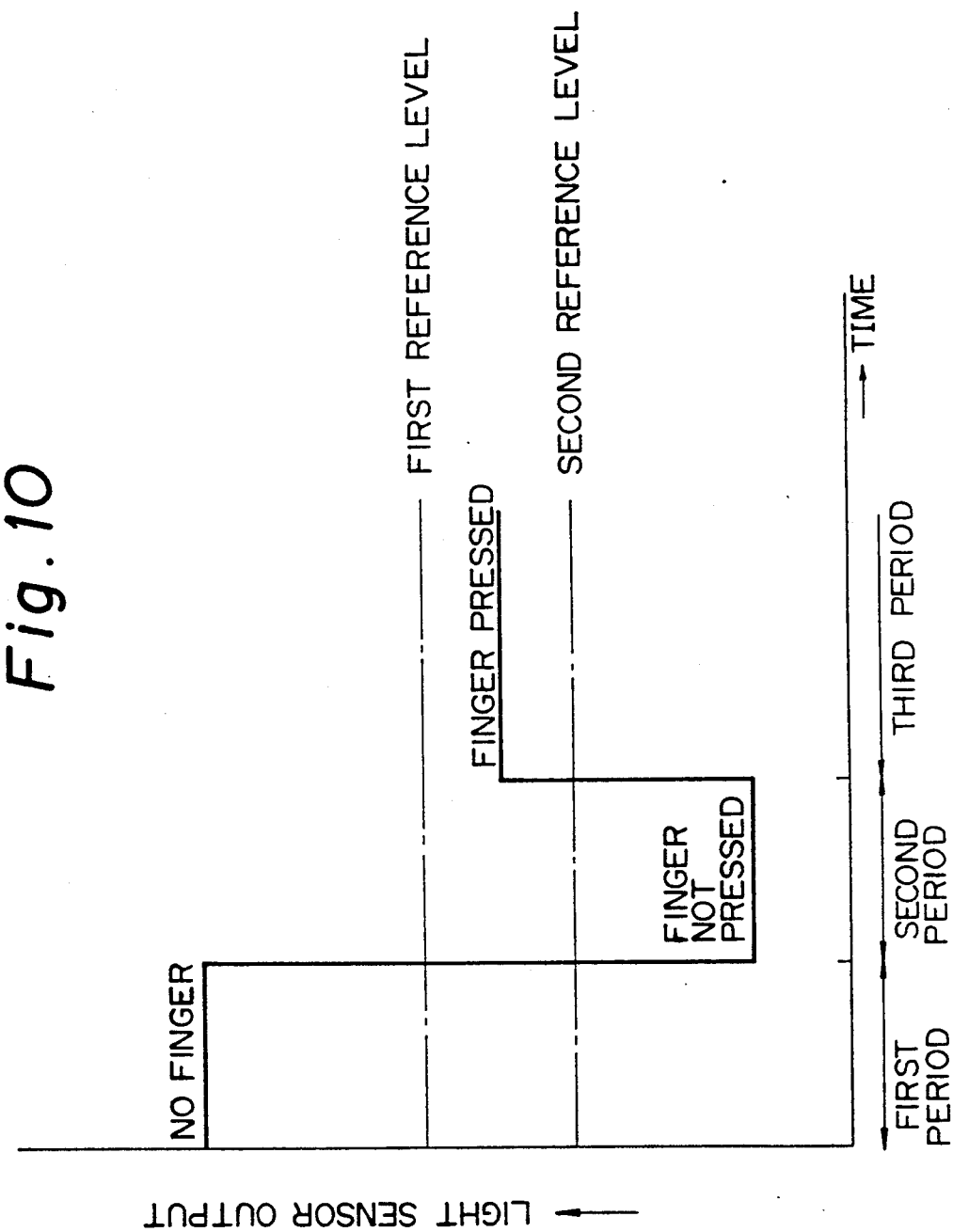
FIG. 10 is a diagram showing the characteristic of the output of the light sensor element in the apparatus of FIG. 9.

The comparator circuit 66 uses a predetermined first reference level, and the comparator circuit 64 uses a predetermined second reference level, in evaluating the characteristic of the output of the light sensor element 533 of FIG. 9A, as shown in FIG. 10. In the sensed light output characteristic as shown in FIG. 10, in the first period during which the finger is not present ("NO FINGER"), the output is at a high level; next in the second period during which the finger is/placed on the plate in the not-pressed state ("FINGER NOT PRESSED), the output is at a low level; and further, in the third period during which the finger is placed on the plate in the pressed state ("FINGER PRESSED), the output is at an intermediate level. The first reference level is selected to be between the high "no finger" level and the intermediate "pressed finger" level, and the second reference level is selected to be between the intermediate "pressed finger" level and the low finger "not-pressed" level.

When the comparator circuits 64 and 66 detect that the sensor output has changed from the "no finger" level to the "not-pressed finger" level, and subsequently, changed from the "not-pressed finger" level to the "pressed finger" level, the one shot multivibrator circuit 65 (FIG. 9A) generates a HIGH level signal which is supplied to the AND circuit 67. The output signal of the comparator 66, which represents the contact of the finger 1 with the glass plate 2, is also supplied to the AND circuit 67. The AND circuit 67 produces the output signal as the biological object detection signal to be supplied to the personal identification unit 43 of FIG. 9B when both the signal from the one shot multivibrator circuit 65 and the signal from the comparator circuit 66 are supplied to the AND circuit 67, i.e., when a genuine biological object is in contact with the plate 2. This operation of the AND circuit 67 cannot be carried out by a fraudulent operation of the fingerprint sensor in which the object under detection is removed from the inspection surface 21 of the plate 2 and replaced by a replica of a finger.

In the personal identification unit 43 (FIG. 9B), the picture receiving portion 431 receives the signal from the light sensing element 42, whereby the light transmitted through the plate 2 and the lens 41 is converted to an electric signal. In the picture storage circuit 432, the picture data from the picture receiving portion 431 is analog-to-digital converted and the converted data is stored therein. Data exchanges are carried out between the picture storage circuit 432 and the binary value forming circuit 433. In the binary value forming circuit 433, the binary value data of the picture data is formed, and in the fine line formation circuit 434, the formation of ridge lines and groove lines is carried out from the binary digital data. In the characteristic (points) extraction circuit 435, the characteristic points are extracted from the picture in the fine line form, and in the angle and crosspoint inspection circuit 437, angles and crosspoints between the lines connecting the branching points or the end points in the characteristic points are extracted. In the adjacent pattern planting circuit 436, a pattern of the binary form adjacent to an end point is separated, based on the output of the angle and crosspoint inspection circuit 437, and the separated pattern is planted adjacent to bridges or interruptions. In the operation control circuit 438, a registration of a personal fingerprint and a comparison of the registered personal fingerprint with the picture input data for fingerprint identification are carried out when the detection of the biological object is confirmed by the receipt of the biological object detection signal from the biological object detection unit 6. The data of the picture processing described above is supplied from the picture storage circuit 432 or the operation control circuit 438 to a CRT display or the like (not shown) for monitoring. In the processing of the picture, the formations of windows by a ten-key or a mouse, and procedures for searching for characteristic points or branching points are carried out. A fraudulent operation of the fingerprint sensor by using a replica of a finger may be displayed on a display device.

As shown in FIG. 10, while the finger is not in contact with the plate 2, the level of the light sensor output is at a high level. At the time immediately after the finger is brought into contact with the plate 2, there is a high blood flow rate through the vein of the finger and the color of the skin of the finger is reddish, and thus the reflectance of the surface of the fingerpad is low. Accordingly, the level of the light sensor output becomes low. After the finger is pressed onto the plate 2, the blood flow rate through the vein of the finger is lowered and the color of the skin of the finger becomes whitish, and thus the reflectance of the surface of the fingerpad is increased. Accordingly, the level of the light sensor reaches an intermediate level.

There is little difference in the reflectance of the surface of the human fingerpad in the high blood flow state and the low blood flow state, for the red spectral wavelength range of light, but there is a great difference in the green spectral wavelength range of light. This is considered to be based on the effect of hemoglobins in the blood.

In the apparatus of FIG. 9, the detection of the biological object is carried out by checking the change with time of the light sensor output from the time at which the finger comes into contact with the plate to the time at which the finger is pressed on the plate, based on the above-described nature of the reflectance of the skin of the human fingerpad.

In the apparatus of FIG. 9, when a replica of a finger made of, for example, silicon plastic, is applied to the plate 2, the change of the reflectance does not occur, and thus the light sensor output is changed from a high level directly to an intermediate level without going through the low level. Therefore, by checking by the biological object detection circuit 6 whether or not the light sensor output has changed through a high level-low level-intermediate level route, it is possible to discriminate a human finger as a biological object from a replica of a finger. Therefore, a fraudulent operation of the fingerprint sensor by first applying a human fingerpad onto the plate 2, and subsequently inserting a replica of finger made of a thin membrane between the human finger and the plate 2 cannot be successful.

In the apparatus of FIG. 9, it is possible to emit the light from the light emitting element directly from the light sensor element 533 in an upward direction. Also, in the biological object detection unit 6 in the apparatus of FIG. 9, it is possible to limit the time of the effectiveness of the biological object detection signal, and accordingly, to dispense with the comparator circuit 66.

((Embodiment of FIG. 11))

An apparatus according to still another embodiment of the present invention is shown in FIG. 11. The apparatus of FIG. 11 is provided with a prism 200 having an inspection surface 201, a light emitting element 3, a lens 541, a filter 542, and light sensor elements 543 and 42'. The output of the light sensor element 543 is supplied to the biological object detection unit, and the output of the light sensor element 42' is supplied to the personal identification unit. The operation of the apparatus of FIG. 11 is similar to that of the apparatus of FIG. 9.

((Embodiment of FIG. 12))

An apparatus according to still another embodiment of the present invention is shown in FIG. 12. The apparatus of FIG. 12 is provided with a transparent plate 2 having an upper surface 21 as the inspection surface, a lower surface 22, and a mirror 23, a diaphragm 451, a spherical surface lens 452, a light sensor element 453 for fingerprint picture image detection, a light emitting element 351, a semitransparent mirror 352, a light conducting transparent member 354, mirrors 355 and 356, a light collecting lens 551, a filter 552, and a light sensor element 553. Each end of the light conducting transparent member 354 is cut to form an oblique surface on which a reflection coating is deposited to form the mirrors 355 and 356.

The light emitting element 351 emits a light including green light of a wavelength of approx. 500 to 550 nm, and the filter 551 allows only light of the green range to pass therethrough.

In the operation of the apparatus of FIG. 12, the change of the value of the green light detected by the light sensor element 553 in a sequence from the time before the contact of the finger with the plate 2 through the coming of the fingerpad into contact with the plate 2, to the pressing of the fingerpad onto the plate 2, is measured.

If this change of the value of the green light shows the characteristic of the change in the green light range shown in FIG. 2, the object on the inspection surface of the plate 2 can be determined to be a human finger as a biological object. If not, the object on the inspection surface of the plate 2 cannot be determined to be a biological object.

In the apparatus of FIG. 12, the light emitting element 351, the semitransparent mirror 352, the light collecting lens 551, the filter 552, and the light sensor element 553 are located above the level of the lower surface 22 of the plate 2, and the light conducting transparent member 354 having the mirrors 355 and 356 is located below the level of the lower surface 22 of the plate 2. Therefore, the distance between the lower surface 22 of the plate 2 and the lower surface 354C of the transparent member 354 can be made as thin as, for example, approx. 5 mm.

In the most preferable arrangement all of the light emitting element 351, the semitransparent mirror 352, the light collecting lens 551, the filter 552, and the light sensor element 553 are included within the thickness of the plate 2. Such an arrangement effectively realizes a fingerprint sensor apparatus having a small thickness.

((Embodiment of FIG. 13))

An apparatus according to still another embodiment of the present invention is shown in FIG. 13. The apparatus of FIG. 13 is provided with a transparent plate 2 having an upper surface 21 as the inspection surface, a lower surface 22, and a mirror 23, a diaphragm 451, a spherical surface lens 452, a light sensor element 453 for fingerprint picture image detection, a light emitting element 351, a light collecting lens 352, a light conducting transparent member 357, reflection type holograms 358 and 359 having a wavelength selection characteristic, and a light sensor element 553.

In the operation of the apparatus of FIG. 13, the change of value of the green light detected by the light sensor element 553 in a sequence from the time before the contact of the finger with the plate 2 through the coming of the fingerpad into contact with the plate 2 to the pressing of the fingerpad onto the plate 2 is measured.

In the apparatus of FIG. 13, the hologram 358 has a wavelength selection characteristic allowing only the green light range to be reflected toward the upper surface of the transparent member 357. The reflected light is fully reflected at the upper surface of the transparent member 357 toward the hologram 359, at which the fully reflected light is reflected upward toward the fingerpad on the plate 2. The reflected light from the surface of the fingerpad is reflected at the hologram 359, fully reflected at the upper surface of the transparent member 357, reflected at the hologram 358, and is detected by the light sensor element 553.

The determination of whether or not the object on the inspection surface of the plate 2 is a human finger as a biological object, based on the detection by the light sensor element 553 in the apparatus of FIG. 13, is similar to that in the apparatus of FIG. 12.

In the apparatus of FIG. 13, the distance between the lower surface 22 of the plate 2 and the lower surface 357C of the transparent member 357 can be made as thin as, for example, approx. 2 to 3 mm.

((Embodiment of FIG. 14))

An apparatus according to still another embodiment of the present invention is shown in FIG. 14. The apparatus of FIG. 14 is provided with a light emitting element 351 for emitting a light including light in the green light range, a first optical fiber 356, a light expansion lens 357 for expanding the light, a light collecting lens 551, a second optical fiber 554, a filter 552 for passing light of only the green light range, and a light sensor element 553.

The determination of whether or not the object on the inspection surface of the plate 2 is a human finger as a biological object, based on the detection by the light sensor element 553 in the apparatus of FIG. 14, is similar to that in the apparatus of FIG. 12.

In the apparatus of FIG. 14, the distance between the lower surface 22 of the plate 2 and the lower end of the second optical fiber 554 can be made as thin as, for example, approx. 5 mm.

((Embodiment of FIG. 15))

An apparatus according to still another embodiment of the present invention is shown in FIG. 15. The apparatus of FIG. 15 is provided with a light emitting element 351, a semitransparent mirror 352, a light conducting transparent plate 354, mirrors 355 and 356, a light collecting lens 551, a filter 552, a light sensor element 553, and a light switch unit 7 having a light source element 71 and a light receiving element 72, In the apparatus of FIG. 15, the presence of the object on the plate 2 is detected by using a light transmitted from the light source element 71 to the light receiving element 72.

Instead of the light guiding structure using a light conducting transparent member with mirrors, it is possible to use a light guiding structure using a light conducting transparent member with holograms as shown in FIG. 13 or a light guiding structure using optical fibers as shown in FIG. 14.

Also, instead of locating the light guiding structure directly below the glass plate as shown in FIGS. 12, 13, 14 and 15, it is possible to cut a side of the plate 2 to form an oblique surface and locate the light guiding structure directly below this oblique surface.

((Embodiment of FIG. 16))

An apparatus according to a further embodiment of the present invention is shown in FIG. 16. The apparatus of FIG. 16 is provided with a transparent plate 2 having an upper surface 21 as the inspection surface, a lower surface 22, a mirror 23, a diaphragm 451, a spherical surface lens 452, a light sensor element 81 such as a color charge-coupled device (color CCD) having a red detection element, a blue detection element, and a green detection element for detecting both a fingerprint picture image and a change of color of the skin of the fingerpad, an RGB separation circuit 82, a biological object detection unit 83 having a color shift correction circuit 831, and a color discrimination circuit 832, and a personal identification unit 84 having a fingerprint picture image receiving circuit 841 and a fingerprint comparison circuit 842. In the apparatus of FIG. 16, the light wavelength selection means is incorporated with the fingerprint picture image detecting element.

The red, blue, and green fingerprint signals S(R), S(B), and S(G) from the RGB separation circuit 82 are supplied to the color shift correction circuit 831 and the color shift corrected fingerprint signals generated in the color shift correction circuit 831 are supplied to the color discrimination circuit 832, which functions as the biological object detection circuit for outputting a biological object confirmation signal.

In the color discrimination circuit 832, a change of color of fingerprint picture image between the fingerprint picture image at the moment of contact of an object to be identified with the plate 2 and the fingerprint picture image after the pressing of the object onto the plate 2 is detected, and it is determined whether or not the object is a biological object. The phenomena whereby the color of the ridge line of the fingerprint is reddish when a fingerpad comes into contact with the glass plate 2 and the color of the ridge line of the fingerprint becomes whitish color after the fingerpad is pressed onto the plate 2, is utilized in this detection. The biological object confirmation signal from the color discrimination circuit 832 is supplied to the fingerprint comparison circuit 842 in the personal identification unit 84 to enable the operation of the fingerprint comparison circuit 842.

One of the red, blue, and green fingerprint signals S(R), S(B), and S(G) from the RGB separation circuit 82, for example, the red fingerprint signal S(R), is supplied to the fingerprint picture image receiving circuit 841 in the personal identification unit 84. The fingerprint picture image signal from the fingerprint picture image receiving circuit 841 is supplied to the fingerprint comparison circuit 842. In the fingerprint comparison circuit 842, the identification of the supplied fingerprint picture image is carried out based on the result of comparison.

We claim:

1. An apparatus for optically detecting a biological object based on changes in the color of a specified surface of the biological object due to a change in the pressure exerted on the biological object, the specified surface further being subject to optical detection of a characteristic pattern, said apparatus comprising:
   a transparent plate for receiving thereon the specified surface of an object to be detected, the plate allowing passage therethrough of projected light and reflected light used for optical detection of the biological element;
   a light source located under said transparent plate for projecting a light beam, used for biological object detection, toward a portion of the specified surface of the object as received on the transparent plate; and
   light detection means located below said transparent plate for receiving the light, as projected from said light source and subsequently reflected by the specified surface of the object, when placed on or pressed onto said transparent plate, and for detecting the characteristic of the reflection rate of the received light and producing a corresponding output, the detection of whether or not the detected object is a biological object being based on the detection of the characteristic of the reflection rate of the received light by said light detection means, said light detection means further comprising means for setting a predetermined first reference level relative to the output of the light detection means, and means for setting a predetermined second reference level relative to the output of the light detection means which is lower than the first reference level, the detection of said object on said transparent plate as a biological object being carried out by confirming that, when said object comes into contact with said transparent plate, the output of said light detection means becomes lower than both the first and second reference levels, and with an elapse of time, the output of said light detection means is at a level between the first and second reference levels.

2. An apparatus according to claim 1, further comprising light conducting means and light direction changing means, provided in the path of the light output from said transparent plate, for transmitting the reflected light to said light detection means.

3. An apparatus for optically detecting a biological object based on changes in the color of a specified surface of the biological object due to a change in the pressure exerted on the biological object, the specified surface further being subject to optical detection of a characteristic pattern, said apparatus comprising:
   a transparent plate for receiving thereon the specified surface of an object to be detected, the plate allowing passage therethrough of projected light and reflected light used for optical detection of the biological element;
   a light source located under said transparent plate for projecting a light beam to be used for personal identification of a characteristic pattern on the specified surface of the object received on the plate and for detection of the object as a biological object; and
   light detection means located below said transparent plate for receiving the light projected from said light source and subsequently reflected by the surface of the object, as placed on or pressed onto said transparent plate, and for detecting the characteristic pattern of the specified surface of the placed object and the characteristic of the reflection rate of the received light and for producing respectively corresponding detected pattern and detected reflection rate outputs, said light detection means further comprising means for setting a predetermined first reference level relative to the detected reflection rate output of the light detection means, and means for setting a predetermined second reference level relative to the detected reflection rate output of the light detection means which is lower than the first reference level, the detection of said object on said transparent plate as a biological object being carried out by confirming that, when said object comes into contact with said transparent plate, the detected reflection rate output of said light detection means becomes lower than both the first and second reference levels, and with an elapse of time, the detected reflection rate output of said light detection means is at a level between the first and second reference levels.

4. An apparatus for optically detecting a biological object based on changes in the color of a surface thereof, produced by different levels of pressure exerted on the biological object, the apparatus comprising:
   a transparent plate having first and second parallel surfaces, extending in a first direction between first and second, opposite ends of the plate, the second surface of the transparent plate receiving thereon a specified surface of a biological object to be detected, the biological object being alternately placed on and pressed onto the second surface of the transparent plate thereby to change the level of pressure exerted thereon and correspondingly to change the color of the specified surface thereof;
   light source means for projecting a light beam, in a second direction substantially transverse to the first direction and in a first sense, onto the first transparent plate surface, the transparent plate transmitting the light beam as thus projected thereon to the second surface thereof and the light beam being reflected from the second surface and transmitted through the transparent plate and emitted from the first surface thereof, substantially in the second direction and in a second, opposite sense, the reflected light beam having different wavelength characteristics corresponding to the different colors of the biological object surface when respectively placed on and pressed onto the second transparent plate surface; and light detection means for receiving the reflected light beam as emitted from the first surface of the transparent plate and detecting the change in the wavelength characteristics of the reflected and received light beam corresponding to the biological object being, alternatively, placed on and pressed onto the second transparent plate surface, the light detection means further comprising means for setting a predetermined first reference level relative to the output of the light detection means, and means for setting a predetermined second reference level relative to the output of the light detection means which is lower than the first reference level, the detection of said object on said transparent plate as a biological object being carried out by confirming that, when said object comes into contact with said transparent plate, the output of said light detection means becomes lower than both the first and second reference levels, and with an elapse of time, the output of said light detection means is at a level between the first and second reference levels.

5. An apparatus as recited in claim 4, wherein the light detection means comprises:

first and second light detection elements, each receiving the reflected light and respectively being responsive to relatively longer and relatively shorter light wavelengths within the spectrum of wavelengths of the light beam projected by the light source means and producing corresponding first and second electrical outputs representative of the intensity of the reflected and received light in the corresponding relatively longer and relatively shorter wavelengths.

6. An apparatus as recited in claim 5, wherein:

said first light detection element is sensitive to light primarily in the red spectral wavelengths; and said second light detection element is sensitive to light in the range of from green to blue spectral wavelengths.

7. An apparatus as recited in claim 5, wherein:

said first light detection element is sensitive to light having a spectral wavelength of from 640–770 nm; and said second light detection element is sensitive to light in the range of spectral wavelengths of from 430–550 nm.

8. An apparatus for optically detecting a biological object based on the change in the color of a surface thereof, produced by different levels of pressure exerted on the biological object, the apparatus comprising:

a transparent plate having first and second parallel surfaces, extending in a first direction between first and second, opposite ends of the plate, the second surface of the transparent plate receiving thereon a specified surface of a biological object to be detected, the biological object being alternately placed on and pressed onto the second surface of the transparent plate thereby to change the level of pressure exerted thereon and correspondingly to change the color of the specified surface thereof;

light source means for projecting a light beam, in a second direction substantially transverse to the first direction and in a first sense, onto the first transparent plate surface, the transparent plate transmitting the light beam as thus projected thereon to the second surface thereof and the light beam being reflected from the second surface and transmitted through the transparent plate and emitted from the first surface thereof, substantially in the second direction and in a second, opposite sense, the reflected light beam having different wavelength characteristics corresponding to the different colors of the biological object surface when respectively placed on and pressed onto the second transparent plate surface; and light detection means for receiving the reflected light beam as emitted from the first surface of the transparent plate and detecting the change in the wavelength characteristics of the reflected and received light beam corresponding to the biological object being, alternately, placed on and pressed onto the second transparent plate surface, the light detection means further comprising:

first and second light detection elements, each receiving the reflected light and respectively being responsive to relatively longer and relatively shorter light wavelengths within the spectrum of wavelengths of the light beam projected by the light source means and producing corresponding first and second electrical outputs representative of the intensity of the reflected and received light in the corresponding relatively longer and relatively shorter wavelengths;

means for setting a first predetermined reference level, lower than the known level of the first electrical output of the first light detection element produced thereby in response to a biological object being placed on the second surface of the transparent plate;

means for receiving the first electrical output and the first predetermined reference level and producing a first detection output in response to the level of the first electrical output of the first light detection element exceeding the first predetermined reference level;

means for receiving and comparing the first and second electrical outputs of the respective, first and second light detection elements and producing a second detection output when the level of the second electrical output is substantially equal to the level of the first electrical output; and third means for receiving the first and second level detection outputs and producing a third detection output in response to the simultaneous and continuing presence of both the aforesaid first and second detection outputs, the third detection output comprising the biological object detection output.

9. An apparatus for optically detecting a biological object based on the change in the color of a surface thereof, produced by different levels of pressure exerted on the biological object, the apparatus comprising:

a transparent plate having first and second parallel surfaces, extending in a first direction between first and second, opposite ends of the plate, the second surface of the transparent plate receiving thereon a specified surface of a biological object to be detected, the biological object being alternately placed on and pressed onto the second surface of the transparent plate thereby to change the level of pressure exerted thereon and correspondingly to change the color of the specified surface thereof;

light source means for projecting a light beam, in a second direction substantially transverse to the first direction and in a first sense, onto the first transparent plate surface, the transparent plate transmitting the light beam as thus projected thereon to the second surface thereof and the light beam being reflected from the second surface and transmitted through the transparent plate and emitted from the first surface thereof, substantially in the second direction and in a second, opposite sense, the reflected light beam having different wavelength characteristics corresponding to the different colors of the biological object surface when respectively placed on and pressed onto the second transparent plate surface; and light detection means for receiving the reflected light beam as emitted from the first surface of the transparent plate and detecting the change in the wavelength characteristics of the reflected and received light beam corresponding to the biological object being, alternately, placed on and pressed onto the second transparent plate surface, the light detection means further comprising:

means for setting a first predetermined reference level corresponding to the level of reflected light received thereby in the absence of any object being received on the second surface of the transparent plate;

means for setting a second predetermined reference level relative to the known characteristics of the detected level of the reflected and received light beam when a biological object is alternately placed on or pressed onto the second surface of the transparent plate; and means for comparing the detected level of the reflected and received light beam with the first and second predetermined reference levels and producing an output indicating the detection of a biological object, when the detected level of the received and reflected light beam, in time sequence, exceeds the first reference level in a first time period, is less than both of the first and second reference levels in a second time period, and is intermediate the first and second reference levels in a third time period.

10. An apparatus as recited in claim 4, wherein said light source means comprises:

a directional light beam transmitting element having a central portion and first and second integral end portions, the central portion extending in the first direction and defining a first light beam transmitting path therethrough in the first direction, and each of the first and second integral end portions redirecting a light beam received thereby, from one to the other of the first light beam transmitting path in the first direction and a substantially transverse, second light beam transmitting path in the second direction, the first end portion being disposed beyond the first end of the transparent plate and the second end portion being disposed intermediate the first and second ends of the transparent plate, the second end portion redirecting a light beam transmitted through the first light beam transmitting path of the central portion to the second light beam transmitting path and thereby projecting the light beam in the second direction onto the first transparent plate surface, as aforesaid, and receiving the reflected light beam as emitted in the second direction from the second surface of the transparent plate and redirecting same for transmission through the first light beam transmitting path of the central portion;

a light beam source disposed adjacent to and spaced in the first direction from the first end portion of the transparent plate, the second end portion receiving a light beam emitted by the light beam source and redirecting same for transmission through the first light beam transmitting path of the central portion of the directional light beam transmitting element; and the light detection means being disposed adjacent to and spaced in the first direction from the first end of the transparent plate and further being disposed adjacent to and spaced in the second direction from the second end portion of the directional light beam transmitting element, the second end portion redirecting a reflected light beam transmitted through the first light beam transmitting path of the central portion thereof for transmission in the second light beam transmitting path associated therewith and thus in the second direction to be received by the light detection means.

11. An apparatus as recited in claim 10, wherein said directional light beam transmitting element comprises a light conducting transparent member, the first and second end portions thereof respectively comprising obliquely inclined and mirrored surfaces for redirecting a light beam received thereby between the first and second light beam transmitting paths.

12. An apparatus as recited in claim 10, wherein the directional light beam transmitting element comprises:

first and second optical fiber elements, each having a central portion extending parallel to the parallel surfaces of the transparent plate and first and second integral, curved end portions extending from the first direction of the central portion to the second, transverse direction corresponding to the second light beam transmitting paths respectively associated therewith, thereby to redirect a light beam received thereby between the first and second directions, as aforesaid.

13. An apparatus for optically detecting a biological object based on the change in the color of a surface thereof, produced by different levels of pressure exerted on the biological object, the apparatus comprising:

a transparent plate having first and second parallel surfaces, extending in a first direction between first and second, opposite ends of the plate, the second surface of the transparent plate receiving thereon a specified surface of a biological object to be detected, the biological object being alternately placed on and pressed onto the second surface of the transparent plate thereby to change the level of pressure exerted thereon and correspondingly to change the color of the specified surface thereof;

light source means for projecting a light beam, in a second direction substantially transverse to the first direction and in a first sense, onto the first transparent plate surface, the transparent plate transmitting the light beam as thus projected thereon to the second surface thereof and the light beam being reflected from the second surface and transmitted through the transparent plate and emitted from the first surface thereof, substantially in the second direction and in a second, opposite sense, the reflected light beam having different wavelength characteristics corresponding to the different colors of the biological object surface when respectively placed on and pressed onto the second transparent plate surface; and light detection and object identifying means for receiving the light beam as emitted from the first surface of the transparent plate and detecting the change in the wavelength characteristics of the reflected and received light beam corresponding to the biological object being, alternately and in a predetermined sequence, placed on and pressed onto the second transparent plate surface and producing a corresponding output indicating that the object received on the second transparent plate surface is recognized as a biological object, and for identifying the detected and recognized biological object by comparing the image of the biological object as represented by the reflected light beam with a stored image of the known biological object, said light detection means further comprising means for setting a predetermined first reference level relative to the output of the light detection means, and means for setting a predetermined second reference level relative to the output of the light detection means which is lower than the first reference level, the detection of said object on said transparent plate as a biological object being carried out by confirming that, when said object comes into contact with said transparent plate, the output of said light detection means becomes lower than both the first and second reference levels, and with an elapse of time, the output of said light detection means is at a level between the first and second reference levels.

14. An apparatus as recited in claim 1 wherein the transparent plate comprises a prism of generally triangular cross-section having a first, upper surface comprising the specified surface on which an object to be detected is received and second and third surfaces extending from respective, opposite edges of the first, upper surface at corresponding first and second acute angles relatively to the first surface, the second and third surfaces intersecting along a common line and defining a third angle.

15. The apparatus of claim 14, wherein the third angle is a right angle.

16. An apparatus for optically detecting a biological object based on changes in the color of a specified surface of the biological object due to a change in the pressure exerted on the biological object, the specified surface further being subject to optical detection of a characteristic pattern, said apparatus comprising:

a transparent prism for receiving thereon the specified surface of an object to be detected, the prism allowing passage therethrough of projected light and reflected light used for optical detection of the biological element;

a light source located under said transparent prism for projecting a light beam, used for biological object detection, toward a portion of the specified surface of the object as received on the transparent prism; and light detection means located below said transparent prism for receiving the light, as projected from said light source and subsequently reflected by the specified surface of the object, when placed on or pressed onto said transparent prism, and for detecting the characteristic of the reflection rate of the received light, the light detection means further comprising means for setting a predetermined first reference level relative to the output of the light detection means, and means for setting a predetermined second reference level relative to the output of the light detection means which is lower than the first reference level, the detection of said object on said transparent prism as a biological object being carried out by confirming that, when said object comes into contact with said transparent prism, the output of said light detection means becomes lower than both the first and second reference levels, and with an elapse of time, the output of said light detection means is at a level between the first and second reference levels.

17. An apparatus as recited in claim 16 wherein the prism is of generally triangular cross-section having a first, upper surface comprising the specified surface on which an object to be detected is received and second and third surfaces extending from respective, opposite edges of the first, upper surface at corresponding first and second acute angles relatively to the first surface, the second and third surfaces intersecting along a common line and defining a third angle.

18. The apparatus of claim 17, wherein the third angle is a right angle.

* * * * *

UNITED STATES PATENT AND TRADEMARK OFFICE
CERTIFICATE OF CORRECTION

PATENT NO. : 5,088,817
DATED : February 18, 1992
INVENTOR(S) : Seigo IGAKI et al.

It is certified that error appears in the above-indentified patent and that said Letters Patent is hereby corrected as shown below:

On the Title Page, insert the following:

--[73] Assignee: Fujitsu Limited, Kawasaki, Japan--.

Col. 2,   line 52,  change "element" to --elements--;
         line 66,  delete "lo".

Col. 3,   line 28,  change "du" to --due--;
         line 35,  delete "a" (second occurrence).

Col. 5,   line 4,   change "sing" to --using--;
         line 18,  change "ns" to --nm--;
         line 22,  delete "a".

Col. 6,   line 16,  change "," to --.--;
         line 18,  after "S(GB)" (first occurrence) insert --, and when the value "S(R)--;
         line 28,  delete ",".

Col. 7,   line 45,  change "=" to --≈--.

UNITED STATES PATENT AND TRADEMARK OFFICE
CERTIFICATE OF CORRECTION

PATENT NO. : 5,088,817
DATED : February 18, 1992
INVENTOR(S) : Seigo IGAKI et al.

It is certified that error appears in the above-indentified patent and that said Letters Patent is hereby corrected as shown below:

Col. 8, line 8, change ", combined as shown in" to --and comprises--;
line 39, delete "/";
line 41, after "PRESSED" insert --"--.
line 43, after "PRESSED" insert --"--.

Col. 12, line 22, change "," to --.--.

Signed and Sealed this

Twelfth Day of July, 1994

Attest:

BRUCE LEHMAN

Attesting Officer        Commissioner of Patents and Trademarks